(12) United States Patent
Reine

(10) Patent No.: US 8,946,467 B2
(45) Date of Patent: Feb. 3, 2015

(54) PROCESS FOR LIQUID PHASE HYDROGENATION OF PHTHALATES

(75) Inventor: Travis Allen Reine, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/805,591

(22) PCT Filed: Jul. 28, 2011

(86) PCT No.: PCT/EP2011/062979
§ 371 (c)(1),
(2), (4) Date: Jan. 15, 2013

(87) PCT Pub. No.: WO2012/038123
PCT Pub. Date: Mar. 29, 2012

(65) Prior Publication Data
US 2014/0148613 A1    May 29, 2014

(30) Foreign Application Priority Data

Sep. 20, 2010   (EP) .................................... 10177626

(51) Int. Cl.
C07C 69/75 (2006.01)
C07C 67/303 (2006.01)
(52) U.S. Cl.
CPC ........... C07C 67/303 (2013.01); *C07C 2101/14* (2013.01)
USPC ....................................................... 560/127
(58) Field of Classification Search
CPC combination set(s) only.
See application file for complete search history.

(56) References Cited

U.S. PATENT DOCUMENTS

| | | |
|---|---|---|
| 5,180,858 A | 1/1993 | Fleckenstein et al. |
| 6,248,924 B1 | 6/2001 | Rühl et al. |
| 6,284,917 B1 | 9/2001 | Brunner et al. |
| 6,888,021 B2 | 5/2005 | Brunner et al. |
| 7,323,597 B2 | 1/2008 | Hugo et al. |
| 7,355,084 B2 | 4/2008 | Böttcher et al. |
| 7,361,714 B2 | 4/2008 | Grass et al. |
| 7,422,904 B2 | 9/2008 | Garton et al. |
| 7,435,848 B2 | 10/2008 | Grass et al. |
| 7,595,420 B2 | 9/2009 | Schlosberg et al. |
| 2006/0149097 A1 | 7/2006 | Soled et al. |
| 2006/0161017 A1 | 7/2006 | Grass et al. |

(Continued)

FOREIGN PATENT DOCUMENTS

| | | |
|---|---|---|
| EP | 1 676 828 | 7/2006 |
| GB | 742931 | 1/1956 |

(Continued)

OTHER PUBLICATIONS

Fogler, H.S., *Elements of Chemical Reaction Engineering*, Recycle Reactors, Prentice-Hall, Inc. 1999, pp. 200-201.

(Continued)

*Primary Examiner* — Jafar Parsa
*Assistant Examiner* — Amy C Bonaparte
(74) *Attorney, Agent, or Firm* — Luke A. Parsons; Leandro Arechederra, III

(57) ABSTRACT

Disclosed is a process for the liquid phase hydrogenation of phthalates to cyclohexanoates. By using a reactor with a multiplicity of tubes, with a cooling fluid supplied to the outside of the tubes, shortcomings of traditional recycle mode fixed bed reactors can be overcome. Feed dilution can be avoided, resulting in much higher reaction rates.

13 Claims, 6 Drawing Sheets

(56) References Cited

U.S. PATENT DOCUMENTS

| | | |
|---|---|---|
| 2006/0167151 A1 | 7/2006 | Grass et al. |
| 2008/0237090 A1 | 10/2008 | Musich et al. |
| 2009/0234152 A1 | 9/2009 | Schlosberg et al. |

FOREIGN PATENT DOCUMENTS

| | | |
|---|---|---|
| GB | 1 396 084 | 5/1975 |
| JP | 5309258 | 11/1993 |
| PL | 138457 | 8/2012 |
| WO | WO97/25136 | 7/1997 |
| WO | WO99/32427 | 7/1999 |

OTHER PUBLICATIONS

E. Talmor, Chevron Research Company, *Two-Phase Downflow Through Catalyst Beds; Part 1. Flow Maps,* AIChE Journal, vol. 23, No. 6, Nov. 1977, pp. 868-874.

US 8,946,467 B2

PROCESS FOR LIQUID PHASE HYDROGENATION OF PHTHALATES

CROSS REFERENCE TO RELATED APPLICATIONS

This application is a 371 National Stage Application of International Application No. PCT/EP2011/062979, filed Jul. 28, 2011 that claims the benefit of EP 10177626.8, filed Sep. 20, 2010, the disclosures of which are incorporated by reference in their entirety.

FIELD OF INVENTION

The invention relates to the liquid phase hydrogenation of phthalates to cyclohexanoates.

DESCRIPTION OF PRIOR ART

The liquid phase hydrogenation of phthalates to cyclohexanoates is typically carried out over a fixed bed of catalyst. The reaction is highly exothermic, but high temperatures in the reactor cause side reactions, which lead to the formation of by-products. Those by-products can affect the performance of the cyclohexanoate product. The by-products typically exhibit similar volatility to the product and may therefore be difficult to separate from the product. Thus it is desirable to control the temperature of the reactor in a narrow, low temperature window.

Traditionally, that temperature control has been achieved by co-feeding an inert diluent stream to the reactor along with the phthalate feed. The inert diluent acts as a heat sink for the heat released by the exothermic reaction. The temperature may be regulated by controlling the ratio of diluent to feed fed to the reactor. It is typical to use a recycle of the reactor product as the diluent stream.

U.S. Pat. No. 7,361,714 B2 describes processes for carrying out phthalate hydrogenation. The use of a solvent as a diluent to improve temperature control and limit the concentration of aromatic compounds is preferred.

U.S. Pat. No. 7,435,848 B2 and US 2006/0161017 A1 also describe processes for carrying out phthalate hydrogenation. A tube bundle reactor can be used. Again, use of a solvent to limit the aromatics concentration is preferred. The aromatics concentration can also be set by the recycle ratio of reactors in loop mode.

Further processes for carrying out phthalate hydrogenation are also disclosed in U.S. Pat. No. 6,284,917 B1 and U.S. Pat. No. 6,888,021 B2. Diluent quantities of from 1 to 30 times the weight of the phthalate are envisaged.

Tube bundle reactors are known in the art. For example, WO9725136 describes a shell-and-tube reactor for exothermic reactions where only a small proportion of the reactants fed in fact undergo a reaction. The selective hydrogenation of acetylene in the presence of olefins is such a reaction.

JP5309258 discloses a shell-and-tube reactor for adding hydrogen to cyclopentadiene, which is diluted to a concentration of 15% in toluene.

PL138457 discloses a shell and tube reactor for benzene hydrogenation. All of the reactants are in the gas phase.

US20080237090 discloses a shell-and-tube reactor for olefin saturation. The cooling fluid is a boiling water.

GB742931 discloses a shell-and-tube reactor for gas-liquid reactions. Catalytic reactions are not mentioned.

U.S. Pat. No. 7,323,597 describes xylylenediamine production in a tube bundle reactor. A portion of the effluent is recycled to help with temperature control.

U.S. Pat. No. 5,180,858 describes the hydrogenation of liquid fatty acid methyl esters. The reaction occurs under trickle flow.

Since the phthalates feed is a liquid and the hydrogen feed is a gas, the reactor is operating in two-phase flow. The hydrodynamic performance of the reactor can therefore also be considered. Improperly designed reactors may experience local areas in the fixed bed of catalyst that are not in contact with the liquid phase. In those areas, the catalyst may dry out, leading to a loss in reactivity of the bed. One way to compensate for such losses is to provide additional reactor volume, with associated higher equipment costs. Increased temperature or a cut back of feed rate may compensate for the losses, but can result in a loss in production capacity or quality. Hydrodynamic design flaws may also result in a reactor experiencing oscillating periods of high and low gas rates. Such a flow regime can result in unstable periods of high and low reaction rates, leading to difficulties in heat removal and managing reactor upsets and creating problems in reactor process control. The quantity of inert diluent affects the hydrodynamic performance of the reactor.

E. Talmor, AIChE Journal, Vol. 23, No 6, pp 868-874 derived a pair of variables that allow the prediction of the type of flow regime of gas-liquid flow over a fixed bed of particles. U.S. Pat. No. 7,422,904 B2 disclosed that those variables could be used in the hydrodynamic design of reactors.

A drawback of the diluent approach is that robust thermal and hydrodynamic reactor design typically requires large recycle ratios. That increases the equipment cost due to increased size of recycle pumps, heat exchangers and associated piping. In addition, the resulting dilution of the reactant reduces the concentration driving force for reaction, leading to slower reaction rates.

The present invention seeks to ameliorate at least some of the above-mentioned problems.

STATEMENTS OF INVENTION

According to a first embodiment of the present invention, there is provided a process for the liquid phase hydrogenation of phthalates to cyclohexanoates, the process comprising:
(a) feeding a liquid feed comprising phthalates and a gas feed comprising hydrogen to a multiplicity of tubes containing a catalyst;
(b) converting at least part of the phthalates to cyclohexanoates in the tubes; and
(c) supplying a cooling fluid to the outside of the tubes so as to maintain the temperature in the tubes in a desired range.

The temperature inside the tubes should be high enough to promote a fast reaction, but not so high that unwanted by-products form. Examples of undesirable by-products include phthalides and 1-2 cyclohexane dicarboxylic acids. Temperature control of phthalate hydrogenation may be particularly challenging, because the reaction is highly exothermic. The temperature in the tubes may be within a range from 90° C. to 170° C. Preferably the temperature in the tubes is within a range from 90° C. to 160° C., more preferably from 90° C. to 150° C., even more preferably from 90° C. to 130° C. and yet more preferably from 105° C. to 120° C.

By using a reactor with a multiplicity of tubes, with a cooling fluid supplied to the outside of the tubes, many of the shortcomings of the traditional recycle mode fixed bed reactor can be overcome. No dilution of the feed is required since the reaction heat can be sufficiently removed as the reaction progresses via heat transfer to the cooling fluid. By avoiding feed dilution, the reactant concentration is maximised, resulting in much higher reaction rates than possible with a diluted feed. For example, the liquid feed may comprise from 90 to 100% phthalates, preferably from 95 to 100% phthalates, more preferably from 99 to 100% phthalates.

Higher reaction rates mean smaller reactor volumes are necessary to achieve the same conversion, leading to capital cost savings. Additional equipment cost savings may also be realised because the peripheral equipment necessary for the recycle stream like pumps, heat exchangers and associated piping can be omitted from the capital inventory.

Preferably the multiplicity of tubes comprises greater than 100, more preferably greater than 200 tubes. For example, the multiplicity of tubes may comprise between 100 and 300, or between 100 and 200 tubes. Preferably the tubes have an external diameter of from 30 to 50 mm and more preferably from 40 to 45 mm. For example, the tubes may have an external diameter of 44 mm. In that case, the internal diameter of the tubes may be 38 mm.

Preferably the liquid feed is not mixed with a diluent stream. In traditional systems the liquid feed is mixed with a diluent, for example recycled product or a solvent, to act as a heat sink. That is, the diluent absorbs some of the heat of reaction, resulting in a lower temperature increase for the reactor contents. In the present invention the liquid feed preferably makes a single pass through the tubes. That is, the liquid feed is not diluted by recycled product being fed back through the reactor. However, although not typically required to remove heat from a well designed reactor in accordance with the invention, the feed may be diluted with an inert stream, such as recycled product, in a class of embodiments. This could be done, for example, when recycle facilities are available due to a retrofit. Dilution could also be used in the case of a highly active fresh catalyst.

The cooling fluid may be a saturated liquid. The liquid would then boil on the tubes and thus cool them. The disadvantage with that technique is that the temperature of the reactor is determined by the boiling point of the liquid, which is controlled by adjusting the pressure of a downstream vapor drum. A commonly and economically available saturated liquid is saturated water. However, controlling the reactor temperature by adjusting the pressure of a steam drum can be difficult when the temperature of the reactor is being maintained in a range close to 100° C. That is because the steam drum must be able to operate at pressures ranging from vacuum to positive pressure during routine operation.

The cooling fluid is therefore preferably a sub-cooled liquid. Sub-cooled liquids are liquids whose temperature is below the saturation temperature of the liquid. The reactor temperature may then be controlled by blending liquids of different temperatures to achieve a cooling fluid temperature setpoint. The pressure may be set to a value high enough to ensure that the liquid does not boil. As an example, the sub-cooled liquid may be sub-cooled water. The temperature set point of the sub-cooled water may be achieved by blending in reactor cooling water or low pressure steam. A further advantage of using a sub-cooled liquid is that in emergency situations, such as temperature runaway, the pressure of the cooling fluid may be reduced until liquid boil-up starts. Under boiling conditions the heat transfer coefficient on the outside of the tubes increases significantly and the available cooling duty is increased accordingly. Thus, the reactor may be brought to a safe condition. A further advantage is that a sub-cooled liquid system is less prone to fouling than a boiling system.

The cooling fluid flows around the outside of the tubes. For example, a 'shell & tube' reactor may be used wherein the tubes are surrounded by a shell and the cooling fluid passes through the shell. The liquid and gas feeds pass along the tubes in the same direction, i.e. co-currently. The cooling fluid may be fed counter-currently to the gas and liquid feeds. However, the cooling fluid is preferably fed co-currently to the gas and liquid feeds. In that way, the largest temperature driving force is at the reactor inlet, where the heat release from the reaction is highest. Thus, the axial temperature profile along the tubes is flattened. Co-current flow may also avoid quenching the reaction at the outlet. Quenching can occur with counter-current flow because the coldest cooling fluid experiences heat transfer with the reactor portion with the lowest volumetric heat release due to the low reactant concentration near the outlet.

Preferably the cooling fluid flow is plug flow. Plug flow can be provided using methods known to those skilled in the art of shell and tube equipment design, such as internals to prevent back-mixing and stimulate good radial distribution. For example, directional flow baffles may be used.

Hydrodynamic design of a reactor comprises balancing the physical design parameters, such as reactor diameter, catalyst packing density and catalyst particle size, with the process design parameters, such as temperature, pressure and gas and liquid flowrates. A flow regime map specifically suited for vapor-liquid phase concurrent flow in fixed beds can be used to aid the design of a fixed bed reactor so as to operate the reactor in the optimum flow regime for high reactor efficiency at low equipment cost. A flow regime map is presented in E. Talmor, AIChE Journal, Vol. 23, No 6, pp 868-874. The volumetric gas to liquid ratio ($\phi$) determines the position on one axis of the map and a ratio between inertia and gravity forces on one hand, and interface and viscous forces on the other, determines the position on the other axis. The latter ratio is represented by the dimensionless parameter $$Ta = \frac{1 + 1/Fr}{We + 1/Re},$$

where Fr is the Froude number, We is the Weber number and Re is the Reynolds number, which are defined in U.S. Pat. No. 7,422,904 B2 and are well know to a person skilled in the art.

There are primarily four flow regimes in which commercial two-phase (vapor-liquid) fixed bed reactors may be operated: gas continuous (spray flow), two continuous phases (trickle flow), alternating gas/liquid continuous (pulsing flow and pulsing/bubbling flow) and liquid continuous (bubble flow). Subsets of these main flow regimes have been identified, and maps in the literature have attempted to draw boundaries between and within the main flow regimes. Often there is some overlap between the regimes, which can be a result of operating hysteresis. In such cases a flow transition occurs at a different point depending on the direction which a process traverses the flow regime map.

Phthalate hydrogenation reactors preferably avoid the predicted flow regime boundary areas. Preferably the reactors maintain a conservative design within a desired flow regime.

The spray regime may be used for phthalate hydrogenation but is not preferred due to the very high gas to liquid volumetric rates required to operate in the gas continuous flow regime. High volumetric gas to liquid flowrates may result in large reactor volumes in order to provide the necessary residence time for the liquid phase reaction.

The trickle flow regime may be used for phthalate hydrogenation. The trickle flow regime is advantageous because it has good mass transfer rates. However, it may be difficult to ensure complete liquid wetting of the entire catalyst surface area, leading to dry spots which reduce the overall catalyst bed effectiveness. It also usually requires a recycle gas compressor.

Pulsing and bubbling flow may be used for phthalate hydrogenation and potentially give very high mass transfer rates. The oscillatory nature of the flow regime may result in non-uniform reaction rates due to catalyst hot spots and unwetted areas, so good control systems may be required. However, in some cases the frequency of the oscillations may be high enough that the oscillations do not affect the control of the reactor, and in some cases may be so high as to be undetectable.

The bubble flow regime may be used for phthalate hydrogenation. The bubble flow regime is advantageous due to the advantages of complete catalyst wetting, absence of flow oscillations and predictable mass transfer rates as a function of gas flow and bubble size.

The flow conditions within the multiplicity of tubes may be controlled by selecting a volumetric ratio between the gas feed flowrate and the liquid feed flowrate that is suitable for the tube diameter, fluid physical properties, pressure and catalyst particle size of the system. Therefore, if the bubble flow regime is desired, the volumetric ratio between the gas feed flowrate and the liquid feed flowrate may be selected such that flow in the multiplicity of tubes is in the bubble flow regime. If the pulsing flow regime is desired, the volumetric ratio between the gas feed flowrate and the liquid feed flowrate may be selected such that flow in the multiplicity of tubes is in the pulsing flow regime. For example, the process conditions may be such that:

$10 < Ta < 500$; and $\{0.045+(0.00035Ta)\} < \phi$.

That would include flows in the bubble and pulsing flow regime. An additional limitation of $\phi < 0.8$ may be used. That would include flows in the bubbling flow regime. The process conditions may include the tube diameter, bed hydraulic diameter, catalyst particle diameter, gas flow rate, liquid flow rate, temperature, pressure, catalyst bed void fraction and the fluid viscosities, densities and surface tensions, all as defined in U.S. Pat. No. 7,422,904 B2. The amount of gas fed to the reactor should be sufficient to achieve the desired stoichiometry, or the desired stoichiometric excess, for phthalate hydrogenation.

In the context of this application, a phthalate may be any ester of phthalic acid. Non-exhaustive examples of phthalates include monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, diisododecyl phthalate, di-n-octadecyl phthalate, diisooctadecyl phthalate, di-n-eicosyl phthalate, monocyclohexyl phthalate, dicyclohexyl phthalate and di-isotridecylphthalate.

The catalyst may be a catalyst suitable for the hydrogenation of phthalates to cyclohexanoates. Suitable catalysts can be found, for example, in U.S. Pat. No. 7,595,420 B2, US 2009/0234152 A1, US 2006/0149097 A1, U.S. Pat. No. 6,248,924 and U.S. Pat. No. 7,355,084.

BRIEF DESCRIPTION OF FIGURES

By way of example only, embodiments of the invention will now be described with reference to the accompanying drawings, of which.

DETAILED DESCRIPTION

Example 1

Figure 1:
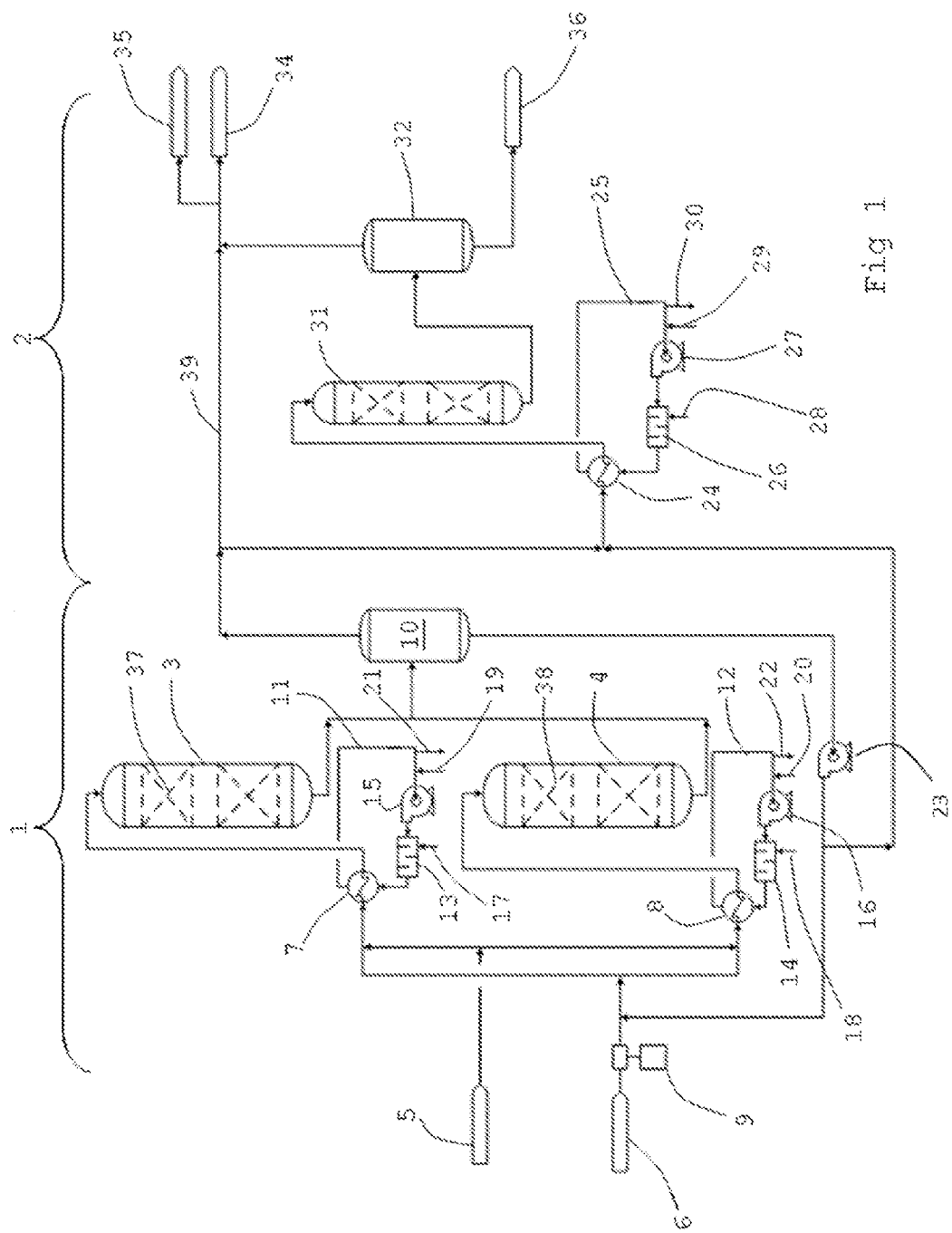
FIG. 1 is a process flow diagram for a phthalate hydrogenation plant.

This example illustrates the use of a flow regime map in the design of a traditional fixed bed reactor with and without a recycle. FIG. 1 is a process flow scheme for a traditional phthalate hydrogenation section. A lead stage 1 consisting of two parallel reactors 3 & 4 operates in recycle mode and a tail stage 2 consisting of a single reactor 31 operates in once-through mode.

The lead stage 1 has fixed bed reactor 3 and fixed bed reactor 4 arranged in parallel. Hydrogen feed 5 and di-isononyl phthalate (herein "DINP") feed 6 are connected to parallel lead reactor conditioners 7 & 8. In the case of the DINP, the connection is via a feed pump 9. The outputs from the conditioners 7 & 8 connect to the top of the reactors 3 & 4 and the outlet of the reactors 3 & 4 is merged before feeding into a flash drum 10. The overhead outlet of the flash drum 10 forms the gaseous feed to the tail section 2, while the bottom outlet is fed to recycle pump 23 and thence partially to the liquid feed to tail section 2 and partially back to the inlets to the conditioners 7 & 8. The conditioners 7 & 8 are each connected to a loop 11 & 12 containing a water mixer 13 & 14 and a water pump 15 & 16. Low pressure steam 17 & 18 and a reactor cooling water supply 19 & 20 can be feed to the loop 11 & 12 and a reactor cooling water return 21 & 22 can be taken out of the loop 11 & 12.

The tail section 2 has a tail conditioner 24, which is in a loop 25 with a water mixer 26 and a water pump 27. Low pressure steam 28 and a reactor cooling water supply 29 can be added to the loop 25 and a reactor cooling water return 30 removed from it. The outlet of the conditioner 24 feeds into the top of a fixed bed reactor 31, the output of which feeds into a flash drum 32. The overhead outlet of the flash drum 32 is merged with a bypass 39 from the overhead outlet of the flash drum 10 and goes to hydrogen recycle compression 34 or offgas fuel 35. The bottoms product from the flash drum 32 goes to finishing 36.

In use, hydrogen from a compressor and DINP from tanks is supplied to the parallel conditioners 7 & 8, where its temperature is adjusted to a desired set-point. The two phase mixture is then fed to the fixed bed reactors 3 & 4, which contain catalyst beds 37 & 38. All reactors are adiabatic fixed beds employing a suitable phthalate hydrogenation catalyst.

Suitable catalysts can be found, for example, in U.S. Pat. No. 7,595,420 B2, US 2009/0234152 A1, US 2006/0149097 A1, U.S. Pat. No. 6,248,924 and U.S. Pat. No. 7,355,084. For example, the catalyst may comprise 0.5 wt % ruthenium on an MCM-41 support. In the reactors 3 & 4 the phthalates are hydrogenated to cyclohexanoates. The product of the two reactors 3 & 4 is merged and fed to a flash drum 10. The overhead product from flash drum 10 forms the gaseous feed to tail section 2. There is a bypass 39 so that the flow of gas to the tail section 2, and hence the hydrodynamic conditions in the tail reactor 31, can be adjusted by controlling the proportion of the flow sent to bypass 39. The bottoms product from flash drum 10 is split to form the recycle and the liquid feed to tail section 2. By controlling the recycle ratio, the liquid flow rate, and hence the hydrodynamic conditions, in the lead section 1 can be adjusted. In the tail section, the gaseous and liquid feeds are combined and fed to conditioner 24 where the inlet temperature to the reactor 31 is set. The tail reactor 31 operates in once through mode so the product passes to flash drum 32, where the bottoms product, which now has a desirably low phthalate content, is sent to finishing and the overhead product goes to hydrogen recycle and offgas fuel.

A simulation based on reaction kinetics, including enthalpy considerations, was used to study the effect of the recycle ratio.

In the lead stage, a recycle ratio of 2.5 can be used to achieve a suitable conversion. The recycle ratio is defined as the total product recycle divided by the total fresh liquid feed. To determine the flow conditions in the reactor, the volumetric gas to liquid ratio and the dimensionless parameter $$Ta = \frac{1 + 1/Fr}{We + 1/Re}$$

are calculated. The resulting position is plotted on the flow map in FIG. 2 to determine the flow regime in which those conditions will result. When the conditions for a recycle ration of 2.5 are plotted on the flow regime map in FIG. 2, the reactor conditions 40a, 40b & 40c at 3 points in the reactor are close to the pulsing flow regime.

Figure 2:
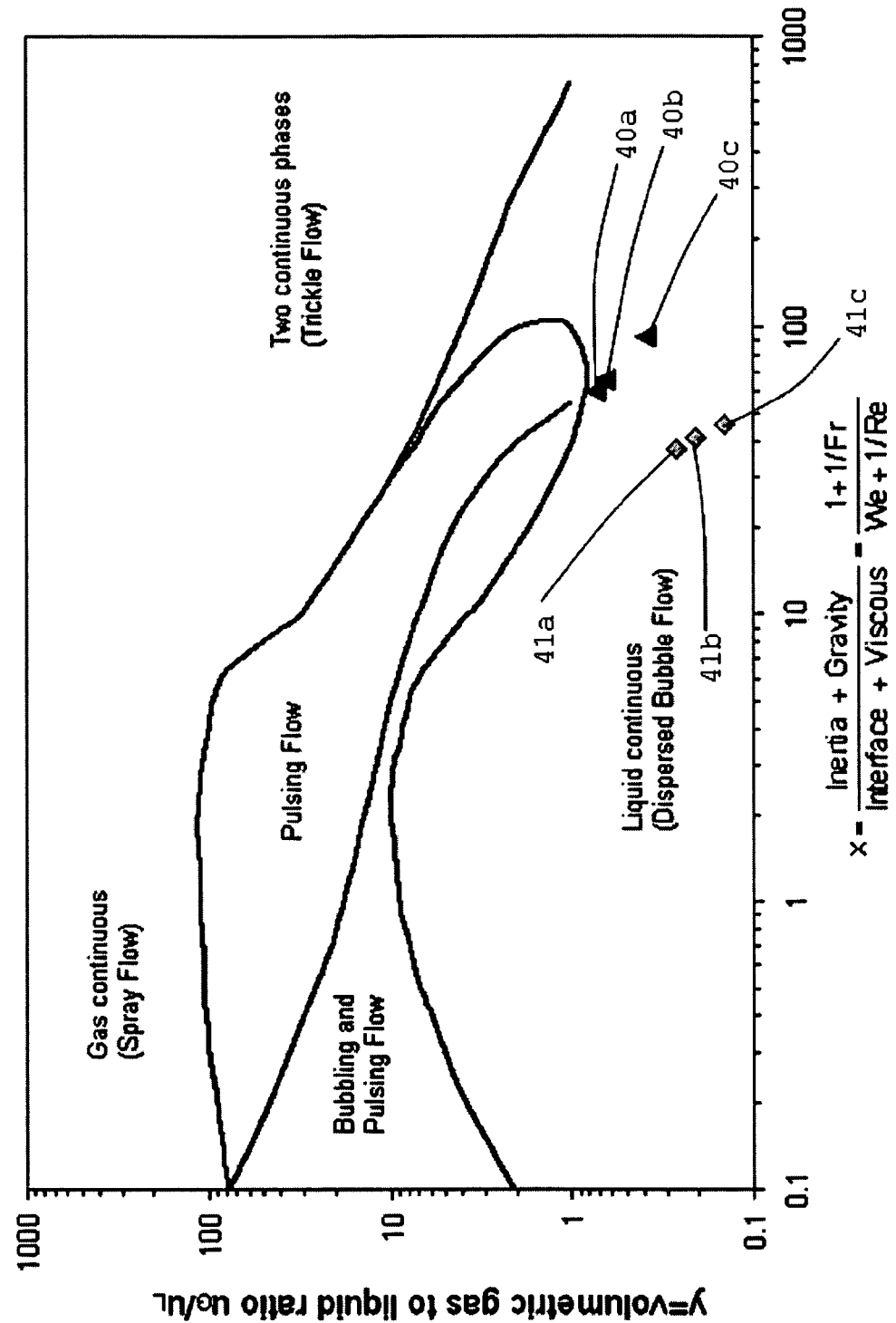
FIG. 2 is a flow regime map used for the design of a part of the plant of FIG. 1.

If the recycle ratio is increased to 10, with the reactor feed temperature setpoint and reactor length adjusted so as to maintain the same degree of conversion and maximum temperature as for the recycle ratio of 2.5 above, the steady state hydrodynamic conditions are in more favorable locations 41a, 41b & 41c on the flow map in FIG. 2. Increasing the recycle ratio has increased the liquid flowrate and moved the reactor hydrodynamic conditions further into the bubble flow regime. There are disadvantages associated with a higher recycle ratio, for example dilution of the phthalate reactant leading to lower reaction rates and larger peripheral equipment such as pumps, heat exchangers, and piping. However, the higher recycle ratio leads to a flatter axial temperature profile in the reactor, which leads to a higher average reaction rate over the entire catalyst bed and therefore a shorter reactor than in the low recycle ratio case above. The higher recycle ratio also provides the stability of operating clearly within the bubble flow regime throughout the length of the reactor.

Thus the flow regime map can be used to optimize the hydrodynamic performance of a traditional fixed bed reactor with a recycle by plotting conditions for various values of key variables and selecting those with a suitable hydrodynamic performance. In this example, conditions have been selected to be within the bubble flow regime. However, in other examples it might be desirable to operate the process to be within another flow regime, such as the pulsing flow regime, or even at or near a regime boundary. The desired flow regime will be selected based on the desired properties of the process, and the map used to ensure that the process falls within the selected regime.

Turning now to the tail section 2, the tail section 2 in FIG. 1 comprises a single fixed bed reactor 31 operating in once-through mode. Very high conversion in the tail reactor 31 can produce a product that can be marketed as "phthalate free". An adiabatic fixed bed reactor may be referred to as a plug flow reactor (PFR). A PFR operated in recycle mode is known to approximate a continuously stirred tank reactor (CSTR) for high recycle rates (see, for example, Carberry, JJ Chemical and Catalytic Reaction Engineering 1976 McGraw-Hill, Inc, Chap. 3, pp 95). Furthermore it is known that a once-through PFR requires less volume to achieve the same conversion as a CSTR (see, for example, Fogler, H. S. Elements of Chemical Reaction Engineering, $3^{rd}$ Ed. 1999 Prentice-Hall, Inc. Example 2-4, pp 46). A once-through PFR may therefore be a preferred reactor for the tail section to achieve high phthalate conversion.

Figure 3:
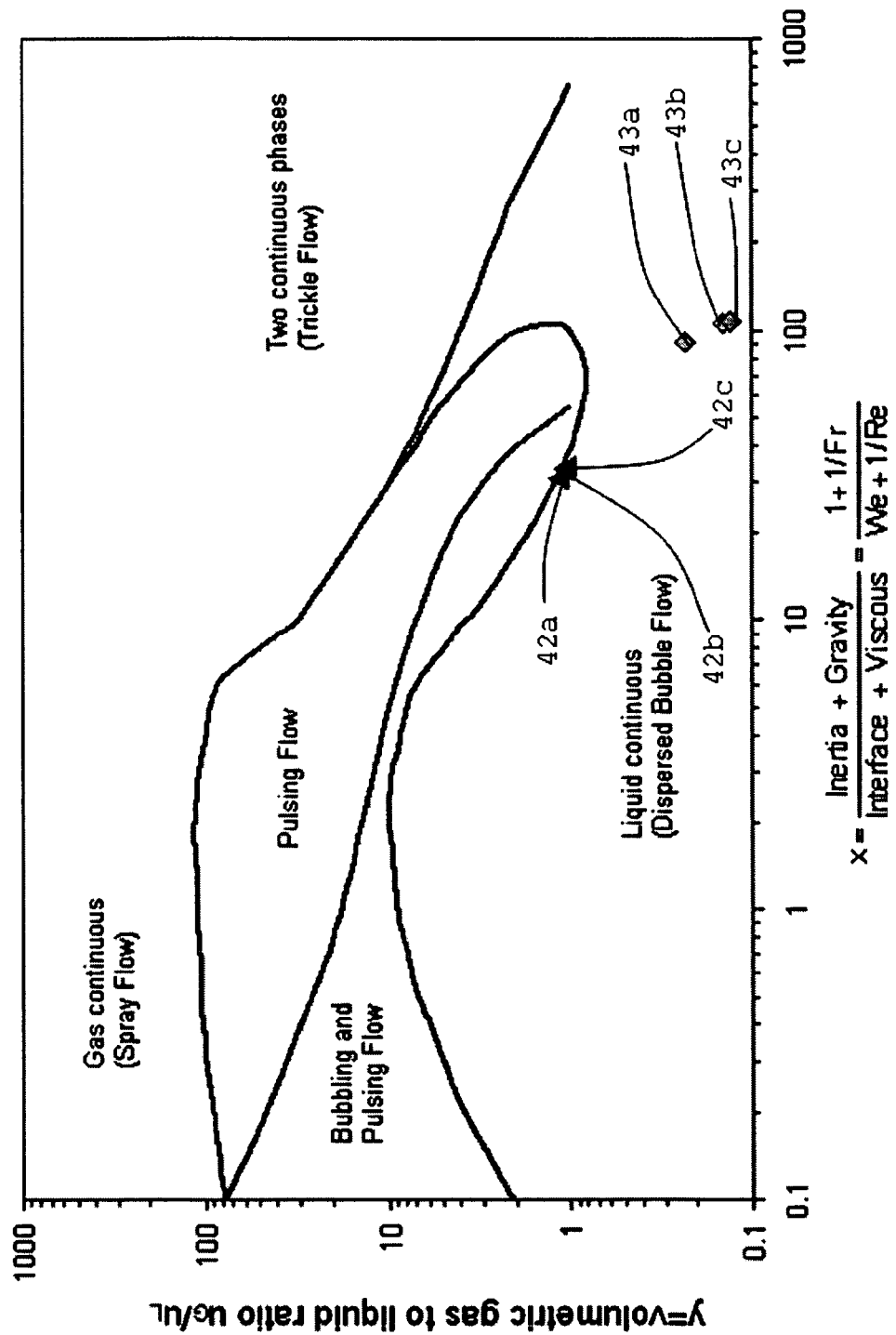
FIG. 3 is a flow regime map used for the design of another part of the plant of FIG. 1.

Even when there is no recycle ratio to adjust, the hydrodynamics of a reactor may still be manipulated by controlling the gas flow rate. In FIG. 1 a 100% excess of stoichiometric hydrogen is fed to the lead reactors 3 & 4. The amount of gas bypassing 39 the tail reactor 31 can then be manipulated to set the gas feed rate to the tail reactor 31. The gas feed rate to the tail reactor 31 may be expressed as a fraction of the total gas stream exiting the lead reactor flash drum 10. If 75% of the flashed gas is fed to the tail reactor 31, the flow regime map in FIG. 3 predicts that the flow conditions 42a, 42b & 42c of the reactor 31 will be near the boundary between the bubble flow and the bubbling/pulsing flow regimes. Reducing the feed to 15% of the flashed gas moves the hydrodynamic conditions 43a, 43b & 43c into the bubble flow regime. Reducing the gas feed alters the gas flow rate relative to the liquid flowrate. The ratio of the gas flowrate to the liquid flowrate may be considered as a key parameter affecting the hydrodynamic flow regime. However, while minimisation of the gas flowrate is beneficial to maintain bubble flow in the tail reactor, the gas flowrate must be kept high enough to ensure that levels of dissolved hydrogen in the reactor 31 are not depleted. That may be achieved by ensuring that there is sufficient gas present throughout the reactor 31 to provide a mass transfer driving force to maintain the required dissolved hydrogen levels in the liquid phase.

Example 2

Figure 4:
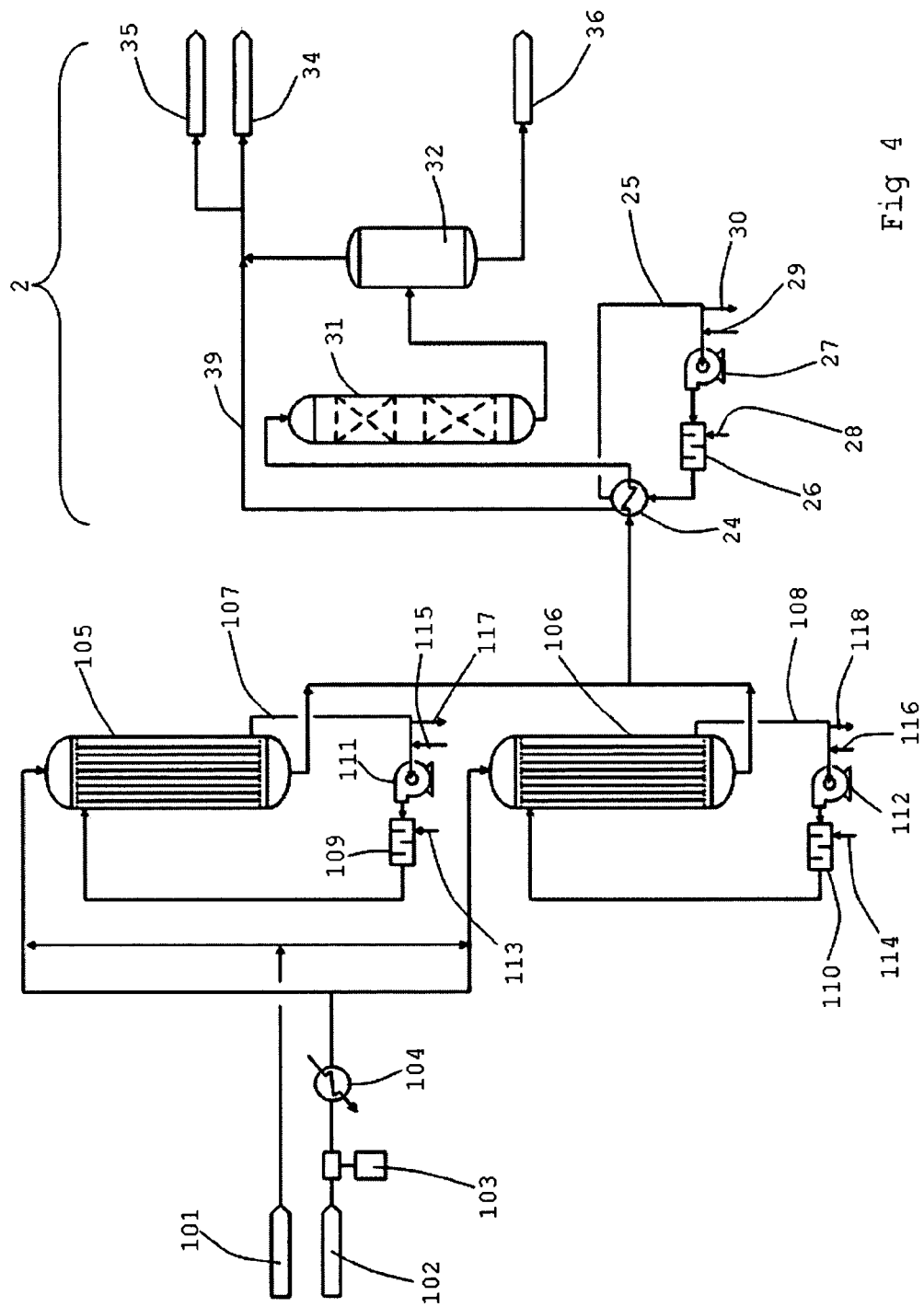
FIG. 4 is a process flow diagram for a phthalate hydrogenation plant embodying the present invention.

This example is directed to a reactor of an embodiment of the invention. In FIG. 4, hydrogen 101 from a compressor and DINP 102 from tanks is mixed and fed to parallel reactors 105 & 106. The DINP is fed via a feed pump 103 and a preheater 104. The reactors 105 & 106 are so-called "shell-and-tube" reactors. The process fluids flow in the tubes and cooling loops 107 & 108 are connected to the shell side. The cooling loops 107 & 108 have water pumps 111 & 112 and water mixers 109 & 110, in which low pressure steam 113 & 114 can be added. A reactor cooling water supply 115 & 116 can also be added to the loops 107 & 108 and a reactor cooling water return 117 & 118 can be removed. The outlets from the reactors 105 & 106 are combined and fed to a tail section 2 as described in relation to example 1.

Figure 5:
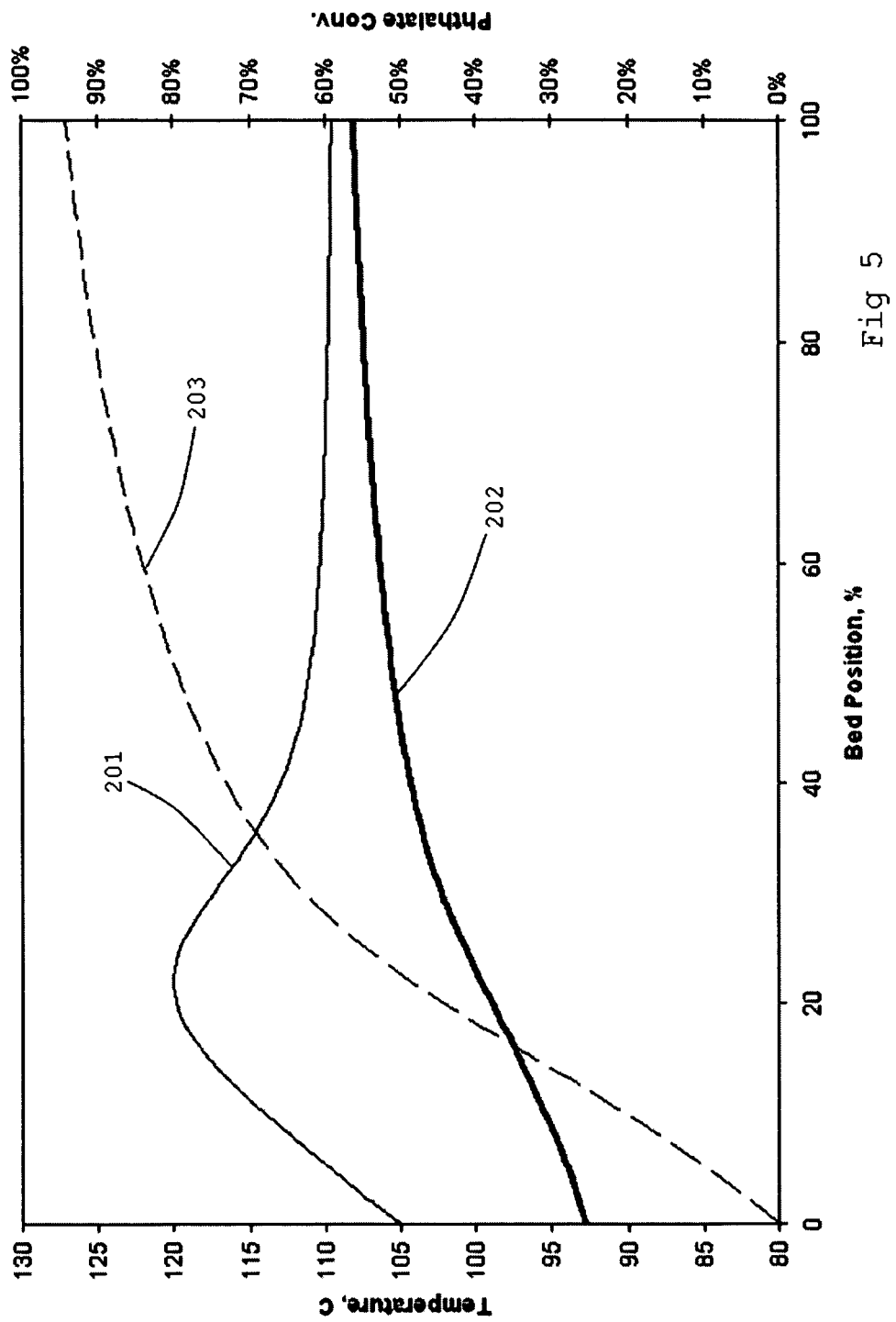
FIG. 5 is a profile of process fluid temperature, cooling water temperature and phthalate conversion for a co-current reactor from the plant of FIG. 4.

The cooling loops 107 & 108 flow co-currently with the gas and liquid feeds through the reactors 105 & 106. FIG. 5 is a plot of the axial temperature profiles for the process fluids 201, and the cooling fluid 202. In this case, the cooling fluid is water. The profiles are plotted as a function of dimensionless reactor length. The phthalate conversion 203 is also plotted. The process temperature is maintained in a window between 105° C. and 120° C. and the phthalate conversion is 93%, which is sufficient to achieve over 99.9% conversion with the use of a tail reactor.

In table 1, the recycle ratio, lead reactor conversion and DINP concentration at the reactor entrance are listed for the fixed bed reactor of example 1 and the shell-and-tube reactor of example 2. Because the shell-and-tube configuration of example 2 does not require a recycle for temperature control purposes, the DINP concentration at the reactor inlet is higher, resulting in faster reaction rates. Faster reaction rates may be beneficial as they may allow smaller reactor sizes, which may result in reduced costs.

TABLE 1

| Reactor | Recycle ratio | Lead reactor conversion | DINP concentration at lead reactor inlet (wt %) |
|---|---|---|---|
| Fixed bed | 2.5 | 93% | 33.3 |
| Fixed bed | 10 | 93% | 15.5 |
| Shell-and-tube | 0 | 93% | 100 |

In table 2, the liquid hourly space velocity (herein "LHSV") and liquid loading of the reactor are compared to the reactor of Example 1 with a recycle ratio of 10. The liquid feed rate and the yield target are the same for both reactors. The LHSV is calculated as the fresh phthalate feed rate divided by the reactor volume and the liquid loading is calculated as the total liquid feed rate (including recycle where present) divided by the cross-section area of the empty reactor. In the case of the shell-and-tube reactor, the cross-section area is that of the process side, that is, the internal cross-section of the tubes. The shell-and-tube reactor has a smaller reactor volume and lower liquid loading than the traditional fixed bed reactor. That leads to potentially lower capital and operating costs for the shell-and-tube reactor.

TABLE 2

|  | Shell-and-tube reactor (Example 2) | Fixed bed in recycle mode (Example 1) |
|---|---|---|
| Phthalate conversion | 93 | 93 |
| LHSV (hr$^{-1}$) | 1.27 | 0.36 |
| Liquid loading (m$^3$/m$^2$ hr) | 18 | 55 |

Example 3

Figure 6:
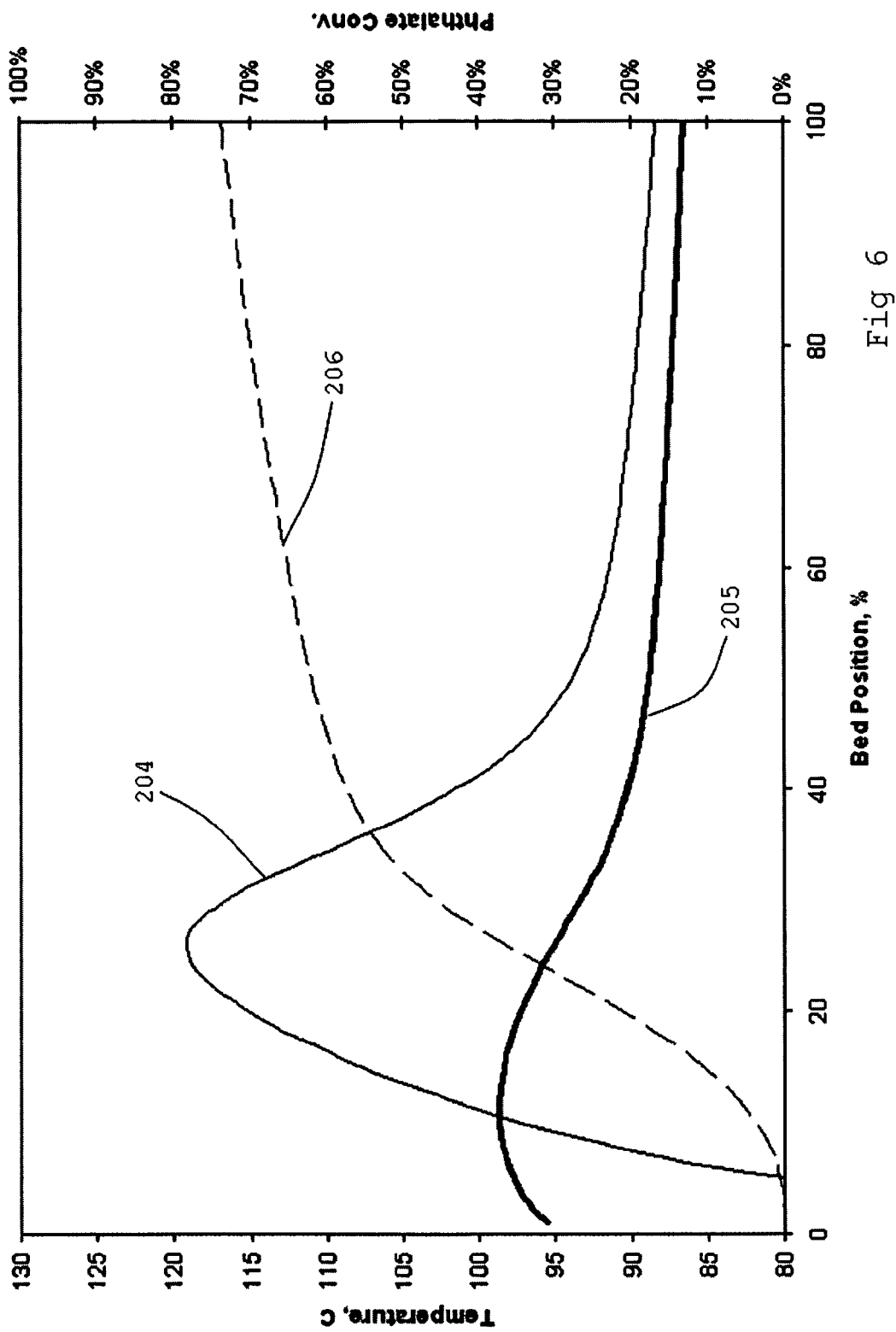
FIG. 6 is a profile of process fluid temperature, cooling water temperature and phthalate conversion for a counter-current reactor from the plant of FIG. 4.

This example uses the same reactor dimensions and cooling water flowrate as Example 2, but the cooling water flows counter-currently to the gas and liquid feeds. The inlet cooling water temperature is varied so as to not allow the maximum process temperature to exceed 120° C. The axial temperature profiles for the process fluid 204 and the cooling fluid 205 are plotted in FIG. 6. The phthalate conversion 206 is also plotted. After about 25% of the reactor length, the temperature of the process reaches a maximum and begins to be reduced by the cooling water, effectively quenching the reaction and limiting phthalate conversion to 71%. The conversion could be increased to the 93% achieved in examples 1 & 2 by increasing the volume of the reactor. However, that would most likely increase capital cost so it may not be desirable dependent on current market conditions.

The invention claimed is:

1. A process for the liquid phase hydrogenation of phthalates to cyclohexanoates, the process comprising:
   (a) feeding a liquid feed comprising phthalates and a gas feed comprising hydrogen to a multiplicity of tubes containing a catalyst;
   (b) converting at least part of the phthalates to cyclohexanoates in the tubes; and
   (c) supplying a cooling fluid to the outside of the tubes so as to maintain the temperature in the tubes in a desired range
   wherein the liquid feed is not mixed with a diluent stream and makes a single pass through the tubes.

2. A process according to claim 1, wherein the temperature is maintained in a range from 90° C. to 170° C.

3. A process according to claim 1, wherein the cooling fluid is subcooled.

4. A process according to claim 1, wherein the cooling fluid is water.

5. A process according to claim 1, wherein the liquid and gas feeds are fed co-currently to the cooling fluid.

6. A process according to claim 1, wherein the liquid and gas feeds are fed counter-currently to the cooling fluid.

7. A process according to claim 1, wherein the tubes are surrounded by a shell and the cooling fluid passes through the shell.

8. A process according to 1, wherein the liquid feed comprises 90 to 100% phthalate.

9. A process according to claim 1, wherein the temperature in the tubes is maintained in a range from 105° C. to 120° C.

10. A process according to claim 1, wherein the volumetric ratio between the gas feed flowrate and the liquid feed flowrate is selected such that flow in the multiplicity of tubes is in the bubble flow regime.

11. A process according to claim 1, wherein the volumetric ratio between the gas feed flowrate and the liquid feed flowrate is selected such that flow in the multiplicity of tubes is in the pulsing flow regime.

12. A process according to claim 1, wherein the process conditions are such that:

$$10 < Ta < 500; \text{ and}$$

$$\{0.045 + (0.00035\,Ta)\} < \phi.$$

13. A process according to claim 12, wherein the volumetric ratio between the gas feed flowrate and the liquid feed flowrate is less than 0.8.

* * * * *

UNITED STATES PATENT AND TRADEMARK OFFICE
CERTIFICATE OF CORRECTION

| | | |
|---|---|---|
| PATENT NO. | : 8,946,467 B2 | Page 1 of 1 |
| APPLICATION NO. | : 13/805591 | |
| DATED | : February 3, 2015 | |
| INVENTOR(S) | : Reine | |

It is certified that error appears in the above-identified patent and that said Letters Patent is hereby corrected as shown below:

In the claims

Claim 8, Column 10, Line 33, insert --claim-- after according to, and before 1.

Signed and Sealed this
Twenty-second Day of March, 2016

Michelle K. Lee
*Director of the United States Patent and Trademark Office*